United States Patent
Ray, II

(10) Patent No.: US 11,701,426 B2
(45) Date of Patent: Jul. 18, 2023

(54) NON-INFECTIVE NASAL SYMPTOM MANAGEMENT COMPOSITIONS AND METHODS

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

(21) Appl. No.: 16/167,108

(22) Filed: Oct. 22, 2018

(65) Prior Publication Data
US 2020/0121795 A1    Apr. 23, 2020

(51) Int. Cl.
| | |
|---|---|
| *A61K 47/18* | (2017.01) |
| *A61K 47/10* | (2017.01) |
| *A61K 31/56* | (2006.01) |
| *A61K 9/00* | (2006.01) |
| *A61K 47/26* | (2006.01) |
| *A61P 37/08* | (2006.01) |
| *A61K 45/06* | (2006.01) |

(52) U.S. Cl.
CPC ............ *A61K 47/18* (2013.01); *A61K 9/0043* (2013.01); *A61K 31/56* (2013.01); *A61K 47/10* (2013.01); *A61K 47/26* (2013.01); *A61P 37/08* (2018.01); *A61K 45/06* (2013.01)

(58) Field of Classification Search
CPC ...... A61K 31/56; A61K 31/573; A61K 31/58; A61K 9/0043; A61K 47/18; A61K 31/522; A61K 2300/00
See application file for complete search history.

(56) References Cited

U.S. PATENT DOCUMENTS

| | | | | |
|---|---|---|---|---|
| 4,003,884 A | * | 1/1977 | Konig | ............... C07K 7/23 530/313 |
| 4,454,140 A | * | 6/1984 | Goldberg | ............ A61K 31/485 514/289 |

FOREIGN PATENT DOCUMENTS

| | | | |
|---|---|---|---|
| CN | 101347436 | * | 1/2009 |
| WO | WO2014205159 | * | 12/2014 |

OTHER PUBLICATIONS

Colak et al., Sugammadex-Induced Hypersensitivity Reaction in a Pediatric Patient. Turk J. Anaesthesiol. Reanim, vol. 46, pp. 66-68, Feb. (Year: 2018).*
May et al., Management of allergic rhinitis: A review for the community pharmacist. Clinical Therapeutics, vol. 39(12), p. 2410-2419, (Year: 2017).*
MedlinePlus Drug Information, Methylprednisolone, last revised Sep. 15, 2017.*
Yuzkat et al., Effects of theophylline with methylprednisolone combination therapy on biomechanics and histopathology in diaphragm muscles of rats. Inflammation, vol. 39(5), pp. 1635-1641, (Year: 2016).*
Mott et al., Topical corticosteroid treatment of anosmia associated with nasal and sinus disease. Arch. Otolaryngol. Head Neck Surg., col. 123(4), pp. 367-372 (Year: 1997).*
The Asthma Center, Smell loss promising New Treatment, Mar. 29, (Year: 2017).*
Wang et al., Comparison of inhaled corticosteroid combined with theophylline and double-dose inhaled corticosteroid in moderate to severe asthma. Respirology, Mar. 31 (Year: 2005).*
Cafasso, What is Anosmia? Updated Aug. 29 (Year: 2019).*
U.S. Pharmacist, Anosmia, US Pharm.vol. 36(1), 17-18 (Year: 2011).*

* cited by examiner

*Primary Examiner* — Barbara P Badio
(74) *Attorney, Agent, or Firm* — Akerman LLP

(57) ABSTRACT

A method of managing non-infective nasal symptoms may include combining a steroid with a diluent, and acetylcysteine, azelastine, or theophylline. The combined ingredients may be mixed to formulate a topical composition for intranasal irrigation or nebulization. The steroid may include fluticasone, budesonide, or methylprednisolone.

14 Claims, No Drawings

NON-INFECTIVE NASAL SYMPTOM MANAGEMENT COMPOSITIONS AND METHODS

FIELD OF THE TECHNOLOGY

The present disclosure is directed to topical composition and related methods of treating non-infective nasal symptoms.

BACKGROUND

Respiratory tract conditions are extremely common ailments of the human experience and include rhinologic conditions, infections, and other obstructions to respiration. One reason for this frequency is constant exposure of respiratory surfaces to the external environment. For example, foreign matter such as debris, microorganisms, viruses, biological matter, and even harsh environmental conditions may enter the body during respiration, irritating or infecting respiratory tract surfaces or even the internal body. Overtime, the human body has also evolved defenses designed to protect the body from this exposure. These defenses include mucous lining and immune responses such as inflammation and increased mucous production or viscosity. Diseases and abnormalities such as chronic obstructive pulmonary disease (COPD), asthma, rhinitis, and various allergies may also include undesirable triggering or modulation of such defenses, e.g., excessive immune responses that cause bronchoconstriction or excessive mucous production or thickening.

Often times an initial treatment objective of respiratory tract conditions is to relieve the obstruction and restore unobstructed respiration by increasing drainage or relieving inflammation. Further objectives may be directed to relieving discomfort or treating the underlying condition. Treatments may include localized application or action of medications, e.g., using nasal spray or metered inhaler. However, respiratory tract conditions may manifest at multiple locations complicating targeted delivery of medication where needed, thus, systemic delivery routes such as oral or intravenous administration, have also been used. Causes of respiratory tract conditions are also numerous and identification of a precise cause may be difficult, especially when multiple conditions are present.

SUMMARY

In one aspect, a method of managing non-infective nasal symptoms includes combining a steroid, theophylline, and a diluent. The method may further include mixing the combined steroid, theophylline, and diluent to formulate a topical composition for intranasal irrigation or nebulization. The steroid may include fluticasone and may be combined in an amount about 0.5 mg to about 6 mg. The steroid may include budesonide and may be combined in an amount about 0.25 mg to about 4 mg. The steroid may include methylprednisolone and may be combined in an amount about 1 mg to about 10 mg. The theophylline may be combined in an amount about 15 mg to about 250 mg.

The method may further include combining poloxamers and xylitol with the steroid, theophylline, and diluent, and mixing the combined poloxamers, xylitol, steroid, theophylline, and diluent. In one embodiment, the diluent comprises distilled water.

In various embodiments, the steroid may be the fluticasone and may be combined in an amount about 3 mg, and the theophylline may be combined in an amount about 100 mg.

In one embodiment, the steroid comprises the budesonide, and the budesonide is combined in an amount about 0.5 mg, about 1 mg, or about 2 mg. In one example, combining the steroid includes combining the contents of one or more budesonide 0.5 mg-2 ml vials and/or one or more budesonide 1 mg-2 ml vials, and the theophylline may be combined in an amount about 100 mg.

In one embodiment, the steroid comprises the methylprednisolone, combined in an amount about 5 mg, and the theophylline is combined in an amount about 100 mg.

The method may further include administering the topical composition to a nasal cavity of a subject via irrigation or nebulization.

In another aspect, a method of managing non-infective nasal symptoms includes combining about 1 mg to about 10 mg methylprednisolone, a diluent, and about 15 mg to about 250 mg acetylcysteine, about 100 mg to about 1 g azelastine, or about 15 mg to about 250 mg theophylline. The method further includes mixing the combined methylprednisolone, diluent, and acetylcysteine, azelastine, or theophylline to formulate a topical composition for intranasal irrigation or nebulization.

The method may further include combining poloxamers and xylitol with the methylprednisolone, diluent, and acetylcysteine, azelastine, or theophylline and mixing the combined poloxamers, xylitol, methylprednisolone, diluent, and acetylcysteine, azelastine, or theophylline. In one formulation, the diluent comprises distilled water.

In one embodiment, the acetylcysteine may be combined in an amount about 100 mg, and the methylprednisolone may be combined in an amount about 5 mg. In another embodiment, the azelastine is combined in an amount about 500 mg, and methylprednisolone is combined in an amount about 5 mg. In still another embodiment, the theophylline is combined in an amount about 100 mg, and the methylprednisolone is combined in an amount about 5 mg.

The method may further include administering the topical composition to a nasal cavity of a subject via irrigation or nebulization.

In still another aspect, a method of managing non-infective nasal symptoms includes combining budesonide, a diluent, and about 15 mg to about 250 mg acetylcysteine, about 100 mg to about 1 g azelastine, or about 15 mg to about 250 mg theophylline. The method further includes mixing the combined budesonide, diluent, and acetylcysteine, azelastine, or theophylline to formulate a topical composition for intranasal irrigation or nebulization. The combining of the budesonide may include combining contents of a budesonide 0.5 mg-2 ml vial or a budesonide 1 mg-2 ml vial. In one example, the combining of the budesonide may include combining the contents of a budesonide 0.5 mg-2 ml vial and a budesonide 1 mg-2 ml vial. In the above or another example, combining the contents of a budesonide vial may include combining the contents of multiple budesonide 0.5 mg-2 ml vials, multiple budesonide 1 mg-2 ml vials, or a combination thereof.

In one embodiment, the diluent comprises distilled water. In some embodiments, the acetylcysteine is combined in an amount about 100 mg, and the budesonide is combined in an amount about 0.5 mg, about 1 mg, or about 2 mg. In another embodiment, the azelastine is combined in an amount about 500 mg, wherein the budesonide is combined in an amount about 0.5 mg, about 1 mg, or about 2 mg. In still another embodiment, the theophylline is combined in an amount about 100 mg, and the budesonide is combined in an amount about 0.5 mg, about 1 mg, or about 2 mg.

DESCRIPTION

The present disclosure describes topical compositions and related methods of treating, e.g., managing, non-infective nasal symptoms. The topical compositions may be formulated for nasal delivery such as irrigation or nebulization, for example. In some applications, the topical compositions may be nasally administered to patients with non-infective nasal issues or medical conditions.

In some embodiments, a topical composition disclosed herein may be used as a supplemental or replacement therapy for patients who are currently using nasally delivered steroids, nasally or orally delivered antihistamines, nasally delivered anticholinergics, nasally or orally delivered mucolytics, orally delivered montelukast, or irrigation systems to clear out the nasal cavities and remove debris. While the topical composition may be formulated for treatment of symptoms generally associated with non-infective nasal conditions, it is contemplated that the topical composition may be used to treat symptoms of a patient, e.g., a mammal, suffering from a nasal/respiratory tract infection as certain symptoms may overlap or otherwise be linked.

Various embodiments of the topical composition may be used to treat one or more of inflammation in nasal cavity, thick-mucus secretions in nasal cavity, allergic rhinitis (runny nose), anosmia (inability to smell), high frequency of nasal infections, or other conditions.

The topical composition and associated methods of treatment may include a pharmaceutically effective amount of an active agent, which those having skill in the art will appreciate may include salts, pharmaceutical equivalents, or derivatives thereof. For brevity, however, such salts, equivalents, and derivatives may be referred to herein with respect to the active agent or class of active agent. For example, the composition may comprise azelastine, which is intended to include an equivalent pharmaceutically effective amount of azelastine hydrochloride.

Various embodiments of the topical composition may include one or more of a steroid, antihistamine, anticholinergic, mucolytic, or combinations thereof.

One or more steroids may include a corticosteroid, glucocorticoid steroid, or both, for example. Corticosteroids mimic the effects of hormones that the body produces naturally in your adrenal glands. Corticosteroids can suppress inflammation and can reduce the signs and symptoms of inflammatory conditions (e.g., arthritis and asthma). Corticosteroids can also suppress the immune system. Corticosteroids can act on a number of different cells (e.g., mast cells, neutrophils, macrophages and lymphocytes) and a number of different mediators (e.g., histamine, leukotriene, and cytokine subtypes).

In various embodiments, the topical composition may include one or more steroids selected from triamcinolone (e.g., diacetate, hexacetonide, and acetonide), betamethasone (e.g., dipropionate, benzoate, sodium phosphate, acetate, and valerate), dexamethasone (e.g., dipropionate and valerate), flunisolide, prednisone (e.g., acetate), prednisolone (e.g., acetate, sodium phosphate, and tebutate), methylprednisolone (e.g., acetate and sodium succinate), fluocinolone (e.g., acetonide), budesonide, diflorasone (e.g., diacetate), halcinonide, desoximetasone (desoxymethasone), diflucortolone (e.g., valerate), flucloronide (fluocortolone acetonide), fluocinonide, fluocortolone, fluprednidene (e.g., acetate), flurandrenolide (flurandrenolone), clobetasol (e.g., propionate), clobetasone (e.g., butyrate), alclometasone, flumethasone (e.g., pivalate), fluocortolone (e.g., hexanoate), amcinonide, beclomethasone (e.g., dipropionate), fluticasone (e.g., propionate), difluprednate, prednicarbate, flurandrenolide, mometasone, and desonide.

In various embodiments, the topical composition includes one or more of the above steroids in an amount about 0.25 mg to about 10 mg, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 2 mg, about 3 mg, about 4 mg, about 5 mg, about 6 mg, or about 7 mg. The amounts of actives, excipients, diluent, and other ingredients disclosed herein with respect to the topical composition may refer to unit dose amounts.

In one embodiment, the steroid comprises or consists of fluticasone. For example, the topical composition may include fluticasone in an amount about 0.5 mg to about 6 mg, about 1 mg to about 5 mg, about 2 mg to about 4 mg, about 2 mg to about 3 mg, about 3 mg to about 4 mg, or about 3 mg.

In one embodiment, the steroid comprises or consists of budesonide. For example, the topical composition may include budesonide in an amount about 0.25 mg to about 4 mg, about 0.25 mg to about 3 mg, about 0.25 mg to about 2 mg, about 0.5 mg to about 2 mg, about 0.5 to about 1 mg, about 1 mg to about 2 mg, about 0.5 mg, about 1 mg, or about 2 mg.

In one embodiment, the steroid comprises or consists of methylprednisolone. For example, the topical composition may include methylprednisolone in an amount about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg. The methylprednisolone may include a methylprednisolone solution, suspension, emulsion, or powder.

The topical composition may include one or more antihistamines. Antihistamines act to reduce or block histamine receptors (e.g., H1 receptors and H2 receptors). Antihistamines include, but are not limited to, the following: acrivastine, azelastine, bilastine, bromodiphenhydramine, brompheniramine, buclizine, carbinoxamine, cetirizine, chlorodiphenhydramine, chlorphenamine, chlorpheniramine, chlorpromazine, cimetidine, clemastine, cyclizine, cyproheptadine, desloratadine, dexbrompheniramine, dexchlorpheniramine, dimenhydrinate, dimetindene, diphenhydramine, doxylamine, ebastine, embramine, emedastine, famotidine, fexofenadine, hydroxyzine, lafutidine, levocabastine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tiotidine, tripelennamine, or triprolidine.

In some embodiments, the topical composition includes any of the steroids and associated amounts of the steroids, identified above or elsewhere herein, and one or more of the above antihistamines in an amount about 10 mg to about 1 g, about 10 mg to about 500 mg, about 15 mg to about 300 mg, about 25 mg to about 300 mg, about 50 mg to about 250 mg, about 75 mg to about 200 mg, about 100 mg to about 900 mg, about 200 mg to about 800 mg, about 300 mg to about 700 mg, about 400 mg to about 700 mg, or about 500 mg to about 800 mg. In one embodiment, the antihistamine comprises or consists of azelastine in an amount about 100 mg to 1000 mg, about 200 mg to about 900 mg, 300 mg to about 800 mg, 400 mg to about 700 mg, 400 mg to about 600 mg, 500 mg to about 600 mg, about 400 mg, about 500 mg, or about 500 mg.

The topical composition may include one or more anticholinergics. Anticholinergics act to block the action of the neurotransmitter acetylcholine in both the central and peripheral nervous systems. In various embodiments, the topical composition includes one or more anticholinergics selected from atropine, belladonna alkaloids, benzatropine, benztropine mesylate, biperiden, bupropion, chlorpheniramine, clemastine, darifenacin, dextromethorphan, dicyclomine, dimenhydrinate, diphenhydramine, doxacurium, doxepin, doxylamine, fesoterodine, flavoxate, glycopyrrolate, hexamethonium, hydroxyzine, hyoscyamine, ipratropium (e.g., ipratropium bromide), mecamylamine, orphenadrine, oxitropium, oxybutynin, procyclidine, propantheline, scopolamine, solifenacin, tiotropium, tolterodine, trihexyphenidyl, tropicamide, tubocurarine, or a combination thereof.

In some embodiments, the topical composition includes any of the steroids and associated amounts of the steroids, identified above or elsewhere herein, and one or more of the above anticholinergics in an amount about 0.01 mg to about 1 mg, about 0.01 mg to about 0.1 mg, about 0.02 mg to about 0.1 mg, about 0.03 mg to about 0.1 mg, about 0.05 mg to about 0.6 mg, about 0.08 mg to about 0.5 mg, about 0.1 to about 0.5 mg, or about 0.5 mg to about 1 mg. In one embodiment, the anticholinergic comprises ipratropium. In some embodiments, the topical composition may include an anticholinergic in addition to the steroid and one or more of an antihistamine, mucolytic, theophylline, anti-inflammatory, or leukotriene receptor antagonist disclosed herein.

The topical composition may include one or more mucolytics. Mucolytics loosen and clear mucus from the airways. The topical composition may include one or more mucolytics selected from acetylcysteine, bromheksin, carbocysteine, erdosteine, guiafenesin, and iodinated glycerol, or pharmaceutically acceptable salts thereof, or a combination thereof.

In some embodiments, the topical composition includes any of the steroids and associated amounts of the steroids, identified above or elsewhere herein, and one or more of the above mucolytics in an amount about 5 mg to about 500 mg, about 15 mg to about 400 mg, about 50 mg to about 300 mg, about 75 mg to about 200 mg, about 75 mg to about 150 mg, about 100 mg to about 250 mg, about 200 mg to about 500 mg. In some embodiments, the topical composition may include a mucolytic in addition to the steroid and one or more of an antihistamine, anticholinergic, theophylline, anti-inflammatory, or leukotriene receptor antagonist. In one embodiment, the mucolytic comprises acetylcysteine in an amount about 15 mg to about 250 mg, about 25 mg to about 200 mg, about 50 mg to about 150 mg, about 75 mg to about 125 mg, or about 100 mg.

The topical composition may include theophylline. Theophylline acts as a phosphodiesterase inhibitor, adenosine receptor blocker, and histone deacetylase activator. Mechanism of action of Theophylline appears to stem from smooth muscle relaxation (bronchodilation) and suppression of the response of the airways to stimuli (i.e. non-bronchodilator prophylactic effects). In some embodiments, the topical composition includes any of the steroids and associated amounts of the steroids identified above and elsewhere herein and theophylline in an amount about 15 mg to about 250 mg, about 25 mg to about 200 mg, about 50 mg to about 150 mg, about 75 mg to about 125 mg, or about 100 mg. In some embodiments, the topical composition may include theophylline in addition to the steroid and one or more of an antihistamine, mucolytic, anticholinergic, anti-inflammatory, or leukotriene receptor antagonist disclosed herein.

In some embodiments, the topical composition may include one or more anti-inflammatories comprising hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide, and non-steroidal anti-inflammatories (NSAIDs) such as salicylate, indomethacin, ibuprofen, diclofenac, flurbiprofen, piroxicam indomethacin, ibuprofen, naxopren, piroxicam and nabumetone. In some embodiments, the topical composition may include any of the steroids and associated amounts of the steroids identified above and elsewhere herein and about 10 mg to about 200 mg anti-inflammatory. In some embodiments, the topical composition may include an anti-inflammatory in addition to the steroid and one or more of an antihistamine, mucolytic, anticholinergic, theophylline, or leukotriene receptor antagonist disclosed herein.

In various embodiments, the topical composition may include one or more leukotriene receptor antagonists. Leukotriene receptor antagonist function as a leukotriene-related enzyme inhibitor or a leukotriene receptor antagonist to oppose the function of these inflammatory mediators. The leukotriene receptor antagonists may include one or more of montelukast, zafirlukast, zilueton, or a combination thereof. In some embodiments, the topical composition may include any of the steroids and associated amounts of the steroids identified above and elsewhere herein and a leukotriene receptor antagonist and one or more of an antihistamine, mucolytic, anticholinergic, theophylline, or anti-inflammatory disclosed herein.

The topical composition may include quinine sulfate. Quinine sulfate may include equivalent amounts of active substance from quinine or other quinine salts such as quinine hydrochloride, quinine di-hydrochloride, quinine sulfate dehydrate, quinine bisulfate, or quinine gluconate. Quinine sulfate is an antimalarial drug indicated only for treatment of uncomplicated Plasmodium falciparum malaria and has been shown to be effective in geographical regions where resistance to chloroquine has been documented. In some embodiments, the topical composition includes any of the steroids and associated amounts of the steroids identified above and elsewhere herein and quinine sulfate in an amount about 50 mg to about 1000 mg, about 50 mg to about 700 mg, about 100 mg to about 700 mg, about 200 mg to about 500 mg, about 300 mg to about 400 mg, about 300 mg to about 700 mg, about 400 mg to about 700 mg, about 500 mg to about 700 mg, about 600 mg to about 700 mg, or about 325 mg or about 650 mg. Quinine sulfate may be combined with any steroid herein. For example, quinine sulfate may be combined with one or more steroids wherein the one or more steroids are present in an amount about 0.25 mg to about 10 mg, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 2 mg, about 3 mg, about 4 mg, about 5 mg, about 6 mg, or about 7 mg. In one embodiment, the steroid comprises or consists of fluticasone, e.g., about 0.5 mg to about 6 mg, about 1 mg to about 5 mg, about 2 mg to about 4 mg, about 2 mg to about 3 mg, about 3 mg to about 4 mg, or about 3 mg fluticasone. In one embodiment, the steroid comprises or consists of budesonide, e.g., for example, about 0.25 mg to about 4 mg, about 0.25 mg to about 3 mg, about 0.25 mg to about 2 mg, about 0.5 mg to about 2 mg, about 0.5 to about 1 mg, about 1 mg to about 1.5 mg, about 1.5 mg to about 2 mg, about 1 mg to about 2 mg, about 0.5 mg, about 1 mg, or about 2 mg budesonide. In one embodiment, the steroid comprises or consists of methylprednisolone, e.g., about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg methylprednisolone.

Quinine sulfate is commercially available in capsules for oral administration. Such capsules may contain 324 mg of the active ingredient quinine sulfate USP, equivalent to 269 mg free base and inactive ingredients: corn starch, magnesium stearate, and talc. Quinine sulfate or quinine sulfate capsules may be available in other capsule strengths. In some embodiments, the topical composition may include in addition to the steroid and one or more of an antihistamine, mucolytic, anticholinergic, anti-inflammatory, or leukotriene receptor antagonist, or theophylline disclosed herein.

The topical composition may comprise one or more of the listed active agents disclosed herein and may further include one or more pharmaceutically acceptable excipients. In other embodiments, however, the formulations consist of the one or more of the listed ingredients and one or more pharmaceutically acceptable excipients. Exemplary excipients may assist in the release, dispersion, solubility, or the delivery of one or more of the active agents or modify taste. For example, excipients may include one or more of diluents, dispersants, preservatives, solvents, co-solvents, wetting agents, buffering agents, humectants, permeation enhancer, emollient, sweetening agents, anti-foaming agents, thickening agents, or flavoring agents, for example. Diluents may include water, distilled water, sterile water, water for injection, sodium chloride, or saline solution, for example. The diluent may comprise an aqueous diluent.

The topical composition may comprise a topical preparation formulated for application to an external or internal body surface such skin or mucosal surfaces of the respiratory tract. The topical compositions may be formulated to act at the tissue surface or absorb for local action. In some embodiments, however, the topical preparations may include an aspect of systemic action.

The topical composition may include an excipient including xylitol, poloxamers, or both. For example, in various embodiments, the topical composition includes a product sold under the name LOXASPERSE, manufactured by PCCA (Houston, Tex.), that includes xylitol and poloxamers.

In some embodiments, the topical composition comprises or consists of a steroid selected from fluticasone, budesonide, methylprednisolone, or combination thereof. For example, the steroid may comprise about 0.5 mg to about 6 mg fluticasone, about 0.25 mg to about 4 mg budesonide, or about 1 mg to about 10 mg methylprednisolone. The topical composition may include a diluent, e.g., as disclosed herein, and optionally one or both of poloxamers or xylitol. For example, poloxamers, xylitol, or mixture thereof may include LOXASPERSE, which may be combined alone or in combination with one or more additional active ingredients.

In one embodiment, the topical composition comprises about 0.5 mg to about 6 mg fluticasone and about 10 mg to about 1 g antihistamine, about 5 mg to 500 mg mucolytic, about 15 mg to 250 mg theophylline. In one example, the antihistamine comprises about 100 mg to about 1 g azelastine. In this or another example, the mucolytic comprises about 15 mg to about 250 mg acetylcysteine. The topical composition may include a diluent, e.g., as disclosed herein, and optionally one or both of poloxamers or xylitol. For example, poloxamers, xylitol, or mixture thereof may include LOXASPERSE, which may be combined alone or in combination with one or more additional active ingredients.

In one embodiment, the topical composition comprises about 0.25 mg to about 4 mg budesonide and about 10 mg to about 1 g antihistamine, about 5 mg to 500 mg mucolytic, about 15 mg to 250 mg theophylline. In one example, the antihistamine comprises about 100 mg to about 1 g azelastine. In this or another example, the mucolytic comprises about 15 mg to about 250 mg acetylcysteine. The topical composition may include a diluent, e.g., as disclosed herein, and optionally one or both of poloxamers or xylitol. For example, poloxamers, xylitol, or mixture thereof may include LOXASPERSE, which may be combined alone or in combination with one or more additional active ingredients.

In one embodiment, the topical composition comprises about 1 mg to about 10 mg methylprednisolone and about 10 mg to about 1 g antihistamine, about 5 mg to 500 mg mucolytic, about 15 mg to 250 mg theophylline. In one example, the antihistamine comprises about 100 mg to about 1 g azelastine. In this or another example, the mucolytic comprises about 15 mg to about 250 mg acetylcysteine. The topical composition may include a diluent, e.g., as disclosed herein, and optionally one or both of poloxamers or xylitol. For example, poloxamers, xylitol, or mixture thereof may include LOXASPERSE, which may be combined alone or in combination with one or more additional active ingredients.

In one embodiment, a method of non-infective nasal symptom management includes nasal administration of topical composition comprising a steroid. The steroid may include one or more steroids selected from, but are not limited to: triamcinolone (e.g., diacetate, hexacetonide, and acetonide), betamethasone (e.g., dipropionate, benzoate, sodium phosphate, acetate, and valerate), dexamethasone (e.g., dipropionate and valerate), flunisolide, prednisone (e.g., acetate), prednisolone (e.g., acetate, sodium phosphate, and tebutate), methylprednisolone (e.g., acetate and sodium succinate), fluocinolone (e.g., acetonide), budesonide, diflorasone (e.g., diacetate), halcinonide, desoximetasone (desoxymethasone), diflucortolone (e.g., valerate), flucloronide (fluclorolone acetonide), fluocinonide, fluocortolone, fluprednidene (e.g., acetate), flurandrenolide (flurandrenolone), clobetasol (e.g., propionate), clobetasone (e.g., butyrate), alclometasone, flumethasone (e.g., pivalate), fluocortolone (e.g., hexanoate), amcinonide, beclometasone (e.g., dipropionate), fluticasone (e.g., propionate), diflupredate, prednicarbate, flurandrenolide, mometasone, and desonide.

In various embodiments, the topical composition or a method of non-infective nasal symptom management may include formulating the topical composition for nasal administration to include a steroid comprising one or more of the above steroids in an amount about 0.25 mg to about 10 mg steroid, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 1.25 mg, about 1.5 mg, about 1.75 mg, about 2 mg, about 3 mg, about 4 mg, about 5 mg, about 6 mg, or about 7 mg. The steroid may include a steroid solution, suspension, emulsion, or powder.

The topical composition may include the diluent or be combined, e.g., added together with the diluent and mixed to form a solution, mixture, emulsion, or suspension, for example, wherein the steroid and/or other active agents are mixed, dissolved, suspended, dispersed, or otherwise within the diluent. The diluent may comprise an aqueous diluent such as water, distilled water, sterile water, water for irrigation, water for injection, saltwater, sodium chloride (e.g., 0.9%) or saline.

The topical composition may be formulated for administration nasally, e.g., by intranasal irrigation or nebulization. In various embodiments, a method of making the topical composition may include mixing the steroid with the diluent. The diluent may be mixed in an amount suitable for the manner of administration. For example, administration volumes for nebulizer solutions may typically range from about 0.2 ml to about 15 ml while irrigation volumes may typically range from about 20 ml to about 500 ml. In an above or another embodiment, the topical composition may include one or both of poloxamers or xylitol. The method may include combining the steroid, and poloxamers, xylitol, or mixture thereof with diluent and mixing. In some embodiments, the poloxamers, xylitol, or mixture thereof includes LOXASPERSE and the method includes also combining the LOXASPERSE with the diluent and steroid and mixing.

In various embodiments, LOXASPERSE may be added in an amount about 100 mg to 1 g, e.g., about 500 mg. Dosing may be 1 to 3 times a day or as otherwise needed.

Combining and mixing may be performed in a mixing container. In some examples, combining and mixing may beneficially be performed within an irrigation system vessel or nebulization vessel.

In various embodiments, the steroid comprises or consists of at least one of fluticasone, budesonide, or methylprednisolone.

In one embodiment, the steroid comprises or consists of fluticasone. For example, the topical composition or the method of non-infective nasal system management may include formulating the topical composition to include fluticasone in an amount about 0.5 mg to about 6 mg, about 1 mg to about 5 mg, about 2 mg to about 4 mg, about 2 mg to about 3 mg, about 3 mg to about 4 mg, or about 3 mg. The fluconazole may include a fluconazole solution, suspension, emulsion, or powder. In one example, to formulate a nebulization or irrigation dosage formulation including 3 mg of fluticasone, the 3 mg of fluticasone powder may be combined with a suitable amount of diluent and mixed. In one embodiment, the diluent comprises distilled water. In one of the above or another embodiment, the topical composition includes one or both of poloxamers or xylitol. The method may include combining the steroid, and poloxamers, xylitol, or mixture thereof with diluent and mixing. In some embodiments, the poloxamers, xylitol, or mixture thereof includes LOXASPERSE and the method includes also combining the LOXASPERSE with the diluent and fluticasone and mixing. In various embodiments, LOXASPERSE may be added in an amount about 100 mg to 1 g, e.g., about 500 mg.

In one embodiment, the steroid comprises or consists of budesonide. For example, the topical composition or the method of non-infective nasal system management may include formulating the topical composition to include budesonide in an amount about 0.25 mg to about 4 mg, about 0.25 mg to about 3 mg, about 0.25 mg to about 2 mg, about 0.5 mg to about 2 mg, about 0.5 mg to about 1 mg, about 1 mg to about 2 mg, about 0.5 mg, about 1 mg, or about 2 mg. The budesonide may include a budesonide solution, suspension, emulsion, or powder.

In various embodiments, the method may comprise combining the contents of one or more commercially available budesonide vials. Budesonide vials contain 2 ml of sterile liquid suspension including 0.25 mg. 0.5 mg, and 1 mg budesonide. Budesonide inhalation suspension, for example, micronized budesonide, sodium chloride, disodium edetate, polysorbate 80, citric acid, tri-sodium citrate, and water for injection. In one example, the method may include combining one or more budesonide 0.5 mg-2 ml vials, 1 mg-2 ml vials, or 1 mg-2 ml vials with a suitable amount of diluent to formulate a nebulization or irrigation dosage formulation and mixing. For example, to formulate a nebulization or irrigation dosage formulation including 0.5 mg budesonide, the contents of a budesonide 0.5 mg-2 ml vial may be combined with diluent and mixed. Similarly, to formulate a nebulization or irrigation dosage formulation including 1 mg budesonide, the contents of a budesonide 1 mg-2 ml vial may be combined with diluent and mixed. Multiples of budesonide vials may also be used to make dosage formulations with higher doses of budesonide than provided by the contents of a vial. In some embodiments, fractions of a vial may also be used for dosage formulations with lower doses of budesonide than provide by the contents of a vial. In one embodiment, the diluent comprises distilled water. In one of the above or another embodiment, the topical composition includes one or both of poloxamers or xylitol. The method may include combining the steroid, and poloxamers, xylitol, or mixture thereof with diluent and mixing. In some embodiments, the poloxamers, xylitol, or mixture thereof includes LOXASPERSE and the method includes also combining the LOXASPERSE with the diluent and budesonide and mixing. In various embodiments, LOXASPERSE may be added in an amount about 100 mg to 1 g, e.g., about 500 mg. In some embodiments, a method of managing non-infective nasal symptoms includes combining budesonide, a diluent, and about 15 mg to about 250 mg acetylcysteine, about 100 mg to about 1 g azelastine, or about 15 mg to about 250 mg theophylline. The method further includes mixing the combined budesonide, diluent, and acetylcysteine, azelastine, or theophylline to formulate a topical composition for nasal administration via intranasal irrigation or nebulization. The combining of the budesonide may include combining contents of one or more budesonide 0.5 mg-2 ml vials or one or more budesonide 1 mg-2 ml vials. In one example, the combining of the budesonide may include combining the contents of one or more budesonide 0.5 mg-2 ml vials and/or one or more budesonide 1 mg-2 ml vials. In the above or another example, combining the contents of a budesonide vial may include combining the contents of multiple budesonide 0.5 mg-2 ml vials, multiple budesonide 1 mg-2 ml vials, or a combination thereof. In one embodiment, the steroid comprises or consists of methylprednisolone. For example, the topical composition or the method of non-infective nasal system management may include formulating the topical composition to include methylprednisolone in an amount about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg. The methylprednisolone may include a methylprednisolone solution, suspension, emulsion, or powder. In one embodiment, the method may comprise combining methylprednisolone powder with a suitable amount of diluent to formulate a nebulization or irrigation solution and mixing. For example, about 5 mg of methylprednisolone powder may be combined with diluent and mixed. In one embodiment, the diluent comprises distilled water. In one of the above or another embodiment, the topical composition includes one or both of poloxamers or xylitol. The method may include combining the steroid, and poloxamers, xylitol, or mixture thereof with diluent and mixing. In some embodiments, the poloxamers, xylitol, or mixture thereof includes LOXASPERSE and the method includes also combining the LOXASPERSE with the diluent and methylprednisolone and mixing. In various embodiments, LOXASPERSE may be added in an amount about 100 mg to 1 g, e.g., about 500 mg.

In one embodiment, the method of non-infective nasal symptom management may include formulating the topical composition to include one or more antihistamines in addition to the one or more of the above steroids in a listed amount. For example, the method may include combining with the steroid one or more antihistamines comprising acrivastine, azelastine, bilastine, bromodiphenhydramine, brompheniramine, buclizine, carbinoxamine, cetirizine, chlorodiphenhydramine, chlorphenamine, chlorpheniramine, chlorpromazine, cimetidine, clemastine, cyclizine, cyproheptadine, desloratadine, dexbrompheniramine, dexchlorpheniramine, dimenhydrinate, dimetindene, diphenhydramine, doxylamine, ebastine, embramine, emedastine, famotidine, fexofenadine, hydroxyzine, lafutidine, levocabastine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tiotidine, tripelennamine, or triprolidine. The antihistamines may be combined in an amount about 10 mg to about 1 g, about 10 mg to about 500 mg, about 15 mg to about 300 mg, about 25 mg to about 300 mg, about 50 mg to about 250 mg, about 75 mg to about 200 mg, about 100 mg to about 900 mg, about 200 mg to about 800 mg, about 300 mg to about 700 mg, about 400 mg to about 700 mg, or about 500 mg to about 800 mg. The antihistamine may include an antihistamine solution, suspension, emulsion, or powder. The antihistamine may be combined and mixed with the steroid and diluent as described above to formulate a topical composition comprising a nebulization or irrigation dosage formulation. In some embodiments, the topical composition may include the antihistamine in addition to the steroid and one or more of a mucolytic, theophylline, anticholinergic, anti-inflammatory, or leukotriene receptor antagonist disclosed herein.

In one embodiment, the antihistamine comprises or consists of azelastine powder in an amount about 100 mg to 1000 mg, about 200 mg to about 900 mg, 300 mg to about 800 mg, 400 mg to about 700 mg, 400 mg to about 600 mg, 500 mg to about 600 mg, about 400 mg, about 500 mg, or about 500 mg.

In one example, a method of making the topical composition comprising a nebulization or irrigation dosage formulation comprising about 500 mg azelastine and about 3 mg fluconazole comprises combining the contents of a capsule containing about 500 mg of azelastine powder with the contents of a capsule containing about 3 mg fluconazole and a suitable amount of diluent, e.g., distilled water, and mixing.

In another example, a method of making the topical composition comprising a nebulization or irrigation dosage formulation comprising about 500 mg azelastine and about 2 mg of budesonide comprises combining the contents of a capsule containing about 500 mg of azelastine powder with the contents of two budesonide 1 mg-2 ml vials and a suitable amount of diluent, e.g., distilled water, and mixing.

In still another example, a method of making the topical composition comprising a nebulization or irrigation dosage formulation comprising about 500 mg azelastine and about 1 mg of budesonide comprises combining the contents of a capsule containing about 500 mg of azelastine powder with the contents of a budesonide 1 mg-2 ml vial, and a suitable amount of diluent, e.g., distilled water, and mixing.

In yet another example, a method of making the topical composition comprising a nebulization or irrigation dosage formulation comprising about 500 mg azelastine and about 0.5 mg of budesonide comprises combining the contents of a capsule containing about 500 mg of azelastine powder with the contents of a budesonide 0.5 mg-2 ml vials and a suitable amount of diluent, e.g., distilled water, and mixing.

In still yet another example, a method of making the topical composition comprising a nebulization or irrigation dosage formulation comprising about 500 mg azelastine and about 5 mg of methylprednisolone comprises combining the contents of a capsule containing about 500 mg of azelastine powder with the contents of a capsule containing about 5 mg of methylprednisolone and a suitable amount of diluent, e.g., distilled water, and mixing.

In one of the above or another embodiment, the topical composition includes steroid, antihistamine, diluent, and one or both of poloxamers or xylitol. The method may include combining the steroid, antihistamine, and poloxamers, xylitol, or mixture thereof with diluent and mixing. In some embodiments, the poloxamers, xylitol, or mixture thereof includes LOXASPERSE and the method includes also combining the LOXASPERSE with the diluent, steroid, and antihistamine and mixing. In various embodiments, LOXASPERSE may be added in an amount about 100 mg to 1 g, for example, about 500 mg. In one example, the LOXASPERSE may be provided in a separate capsule or together with one or both of the steroid or antihistamine or another ingredient. Dosing may be 1 to 3 times a day or as otherwise needed.

In one embodiment, the method of non-infective nasal symptom management may include formulating the topical composition to include one or more mucolytics in addition to the one or more of the above steroids in a listed amount. For example, the method may include combining with the steroid one or more mucolytics comprising selected from acetylcysteine, bromheksin, carbocysteine, erdosteine, guiafenesin, and iodinated glycerol, or pharmaceutically acceptable salts thereof, or a combination thereof.

In some embodiments, the topical composition includes any of the steroids and associate amounts of steroid identified above and elsewhere herein and one or more of the above mucolytics in an amount about 5 mg to about 500 mg, about 15 mg to about 400 mg, about 50 mg to about 300 mg, about 75 mg to about 200 mg, about 75 mg to about 150 mg, about 100 mg to about 250 mg, about 200 mg to about 500 mg. The mucolytic may include a mucolytic solution, suspension, emulsion, or powder. The mucolytic may be combined and mixed with the steroid and diluent as described above to formulate a topical composition comprising a nebulization or irrigation dosage formulation. In some embodiments, the topical composition may include a mucolytic in addition to the steroid and one or more of an antihistamine, anticholinergic, theophylline, anti-inflammatory, or leukotriene receptor antagonist disclosed herein.

In one embodiment, the mucolytic comprises acetylcysteine in an amount about 15 mg to about 250 mg, about 25 mg to about 200 mg, about 50 mg to about 150 mg, about 75 mg to about 125 mg, or about 100 mg.

In one example, a method of making the topical composition comprising a nebulization or irrigation dosage formulation comprising about 100 mg acetylcysteine and about 3 mg fluconazole comprises combining the contents of a capsule containing about 100 mg of acetylcysteine powder with the contents of a capsule containing about 3 mg fluconazole and a suitable amount of diluent, e.g., distilled water, and mixing.

In another example, a method of making the topical composition comprising a nebulization or irrigation dosage formulation comprising about 100 mg acetylcysteine and about 2 mg of budesonide comprises combining the contents of a capsule containing about 100 mg of acetylcysteine powder with the contents of two budesonide 1 mg-2 ml vials and a suitable amount of diluent, e.g., distilled water, and mixing.

In still another example, a method of making the topical composition comprising a nebulization or irrigation dosage formulation comprising about 100 mg acetylcysteine and about 1 mg of budesonide comprises combining the contents of a capsule containing about 100 mg of acetylcysteine powder with the contents of a budesonide 1 mg-2 ml vial, and a suitable amount of diluent, e.g., distilled water, and mixing.

In yet another example, a method of making the topical composition comprising a nebulization or irrigation dosage formulation comprising about 100 mg acetylcysteine and about 0.5 mg of budesonide comprises combining the contents of a capsule containing about 100 mg of acetylcysteine powder with the contents of a budesonide 0.5 mg-2 ml vials and a suitable amount of diluent, e.g., distilled water, and mixing.

In still yet another example, a method of making the topical composition comprising a nebulization or irrigation dosage formulation comprising about 100 mg acetylcysteine and about 5 mg of methylprednisolone comprises combining the contents of a capsule containing about 100 mg of acetylcysteine powder with the contents of a capsule containing about 5 mg of methylprednisolone and a suitable amount of diluent, e.g., distilled water, and mixing.

In one of the above or another embodiment, the topical composition includes steroid, mucolytic, diluent, and one or both of poloxamers or xylitol. The method may include combining the steroid, mucolytic, and poloxamers, xylitol, or mixture thereof with diluent and mixing. In some embodiments, the poloxamers, xylitol, or mixture thereof includes LOXASPERSE and the method includes also combining the LOXASPERSE with the diluent, steroid, and antihistamine and mixing. In various embodiments, LOXASPERSE may be added in an amount about 100 mg to 1 g, for example, about 500 mg. In one example, the LOXASPERSE may be provided in a separate capsule or together with one or both of the steroid or mucolytic or another ingredient. Dosing may be 1 to 3 times a day or as otherwise needed.

In one embodiment, the method of non-infective nasal symptom management may include formulating the topical composition to include theophylline in addition to the one or more of the above steroids in a listed amount. For example, the method may include combining with the steroid theophylline. In some embodiments, the method includes formulating the topical composition to includes any of the steroids and associate amounts of steroid identified above and elsewhere herein and theophylline in an amount about 15 mg to about 250 mg, about 25 mg to about 200 mg, about 50 mg to about 150 mg, about 75 mg to about 125 mg, or about 100 mg. Theophylline may include a theophylline solution, suspension, emulsion, or powder. The theophylline may be combined and mixed with the steroid and diluent as described above to formulate a topical composition comprising a nebulization or irrigation dosage formulation. In some embodiments, the topical composition may include theophylline in addition to the steroid and one or more of an antihistamine, mucolytic, anticholinergic, anti-inflammatory, or leukotriene receptor antagonist disclosed herein.

In one example, a method of making the topical composition comprising a nebulization or irrigation dosage formulation comprising about 100 mg theophylline and about 3 mg fluconazole comprises combining the contents of a capsule containing about 100 mg of theophylline powder with the contents of a capsule containing about 3 mg fluconazole and a suitable amount of diluent, e.g., distilled water, and mixing.

In another example, a method of making the topical composition comprising a nebulization or irrigation dosage formulation comprising about 100 mg theophylline and about 2 mg of budesonide comprises combining the contents of a capsule containing about 100 mg theophylline powder with the contents of two budesonide 1 mg-2 ml vials and a suitable amount of diluent, e.g., distilled water, and mixing.

In still another example, a method of making the topical composition comprising a nebulization or irrigation dosage formulation comprising about 100 mg theophylline and about 1 mg of budesonide comprises combining the contents of a capsule containing about 100 mg of theophylline powder with the contents of a budeosonide 1 mg-2 ml vial, and a suitable amount of diluent, e.g., distilled water, and mixing.

In yet another example, a method of making the topical composition comprising a nebulization or irrigation dosage formulation comprising about 100 mg theophylline and about 0.5 mg of budesonide comprises combining the contents of a capsule containing about 100 mg of theophylline powder with the contents of a budesonide 0.5 mg-2 ml vials and a suitable amount of diluent, e.g., distilled water, and mixing.

In still yet another example, a method of making the topical composition comprising a nebulization or irrigation dosage formulation comprising about 100 mg theophylline and about 5 mg of methylprednisolone comprises combining the contents of a capsule containing about 100 mg pf theophylline powder with the contents of a capsule containing about 5 mg of methylprednisolone and a suitable amount of diluent, e.g., distilled water, and mixing.

In one of the above or another embodiment, the topical composition includes steroid, theophylline, diluent, and one or both of poloxamers or xylitol. The method may include combining the steroid, theophylline, and poloxamers, xylitol, or mixture thereof with diluent and mixing. In some embodiments, the poloxamers, xylitol, or mixture thereof includes LOXASPERSE and the method includes also combining the LOXASPERSE with the diluent, steroid, and theophylline and mixing. In various embodiments, LOXASPERSE may be added in an amount about 100 mg to 1 g, for example, about 500 mg. In one example, the LOXASPERSE may be provided in a separate capsule or together with one or both of the steroid or theophylline or another ingredient. Dosing may be 1 to 3 times a day or as otherwise needed.

In one embodiment, the method of non-infective nasal symptom management may include formulating the topical composition to include quinine sulfate in addition to the steroid, e.g., one or more of the above steroids, in a listed amount. For example, the method may include addition of quinine sulfate with the steroid and theophylline. In some embodiments, the method includes formulating the topical composition to includes any of the steroids and associated amounts of steroid identified above and elsewhere herein and quinine sulfate in an amount about 50 mg to about 1000 mg, about 50 mg to about 700 mg, about 50 mg to about 500 mg, about 50 mg to about 350 mg, about 100 mg to about 325 mg, about 100 mg to about 200 mg, about 200 mg to about 350 mg, about 250 mg to about 325 mg, about 150 mg to about 300 mg, about 275 mg to about 325 mg, about 100 mg to about 700 mg, about 200 mg to about 500 mg, about 300 mg to about 400 mg, about 300 mg to about 700 mg, about 400 mg to about 700 mg, about 500 mg to about 700 mg, about 600 mg to about 700 mg, or about 325 mg or about 650 mg. Quinine sulfate may include a quinine sulfate solution, suspension, emulsion, tablet, capsule, or powder. Quinine sulfate may include commercially available quinine sulfate, e.g., quinine sulfate solution, suspension, emulsion, capsule, table or powder. The quinine sulfate may be combined and mixed with the steroid and diluent as described above to formulate a topical composition comprising a nebulization or irrigation dosage formulation for nasal administration. In some embodiments, the topical composition may include quinine sulfate in addition to the steroid and one or more of an antihistamine, mucolytic, anticholinergic, anti-inflammatory, theophylline, or leukotriene receptor antagonist disclosed herein.

In one example, a method of making the topical composition comprising a nebulization or irrigation dosage formulation comprising up to about 325 mg quinine sulfate and about 3 mg fluconazole comprises combining the contents or an equivalent portion thereof of a 324 mg quinine sulfate capsule with the contents of a capsule containing about 3 mg fluconazole and a suitable amount of diluent, e.g., distilled water or saline solution, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In another example, a method of making the topical composition comprising a nebulization or irrigation dosage formulation comprising up to about 325 mg quinine sulfate and about 2 mg of budesonide comprises combining the contents or equivalent portion thereof of a 324 mg quinine sulfate capsule with the contents of two budesonide 1 mg-2 ml vials and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In still another example, a method of making the topical composition comprising a nebulization or irrigation dosage formulation comprising up to about 325 mg quinine sulfate and about 1 mg of budesonide comprises combining the contents or an equivalent portion thereof of a 324 mg quinine sulfate capsule with the contents of a budesonide 1 mg-2 ml vial, and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In yet another example, a method of making the topical composition comprising a nebulization or irrigation dosage formulation comprising up to about 325 mg quinine sulfate and about 0.5 mg of budesonide comprises combining the contents or an equivalent portion thereof of a 324 mg quinine sulfate capsule with the contents of a budesonide 0.5 mg-2 ml vial and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In still yet another example, a method of making the topical composition comprising a nebulization or irrigation dosage formulation comprising up to about 325 mg quinine sulfate and about 5 mg of methylprednisolone comprises combining the contents or an equivalent portion thereof of a 324 mg quinine sulfate capsule the contents of a capsule containing about 5 mg of methylprednisolone and a suitable amount of diluent, e.g., distilled water, and mixing. Formulations for larger dosages may also be used, e.g., dosages including up to about 650 mg quinine sulfate may be formulated with two 324 mg quinine sulfate capsules. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein.

In one of the above or another embodiment, the topical composition may include steroid, quinine sulfate, diluent, and one or both of poloxamers or xylitol. The method may include combining the steroid, quinine sulfate, and poloxamers, xylitol, or mixture thereof with diluent and mixing. In some embodiments, the poloxamers, xylitol, or mixture thereof includes LOXASPERSE and the method includes also combining the LOXASPERSE with the diluent, steroid, and quinine sulfate and mixing. In various embodiments, LOXASPERSE may be added in an amount about 100 mg to 1 g, for example, about 500 mg. In some embodiments, the method includes combining the contents of one or more compounded capsules including quinine sulfate powder. The quinine sulfate powder may be compounded alone, with steroid, one or more other actives, and/or with xylitol and/or poloxamers. The composition may be delivered nasally as disclosed herein. In one example, the LOXASPERSE may be provided in a separate capsule or together with one or both of the steroid or quinine sulfate or another ingredient. Dosing may be 1 to 3 times a day or as otherwise needed.

The topical composition may comprise one or more of the listed active agents disclosed herein and may further include one or more pharmaceutically acceptable excipients. In other embodiments, however, the formulations consist of the one or more of the listed ingredients and one or more pharmaceutically acceptable excipients. Exemplary excipients may assist in the release, dispersion, solubility, or the delivery of one or more of the active agents or modify taste. For example, excipients may include one or more of diluents, dispersants, preservatives, solvents, co-solvents, wetting agents, buffering agents, humectants, permeation enhancer, emollient, sweetening agents, anti-foaming agents, thickening agents, or flavoring agents, for example. Diluents may include water, distilled water, sterile water, water for injection, sodium chloride, or saline solution, for example. The diluent may comprise an aqueous diluent.

In various embodiments, the method of non-infective nasal symptom management comprises nasal administering of the topical composition. For example, the topical composition may be administered via a spray in a liquid solution or dry powder. In some embodiments, the topical compositions disclosed herein may be formulated without a liquid diluent for nasal administration in a powder format. In some embodiments, nasal administration may also include nasal/intranasal irrigation or nebulization dosage. Accordingly, the topical composition may comprise or be formulated as spray, powder, irrigation, or nebulizer dosage formulation configured for nasal administration. Such formulations may be configured, for example, for delivery to target sites for treatment by spray, irrigation, or nebulization. For example, the topical composition, when prepared for administration, may be formulated in a dose form comprising a treatment solution suitable for administration to the nasal cavity, upper respiratory tract, and in some instances lower respiratory tract. In one embodiment, the topical composition is formulated to be delivered by irrigation at the nasal cavity. In another embodiment, the topical composition is formulated to be delivered by a nebulizer to produce aerosol particles or droplets suitable for inhalation and targeted deposition of such aerosol along the respiratory tract. In some embodiments, the topical composition may be nebulized using a nebulizer configured to produce small or large aerosol particles, with respect to the particle size dispersion generated by the nebulization, e.g., using a NASONEB®, Sinustar, or other suitable nebulizer. Various embodiments may further comprise a fluid, carrier, diluent, which may include delivery vehicles, excipients, or additional active agents.

In one embodiment, the topical composition is formulated into a nebulizer formulation for delivery via a small particle nebulizer device or delivery system. The small particle nebulization delivery system may be configured to nebulize the formulation, e.g., solution, to produce small particles or droplets, e.g., having aerosol characteristics, wherein the particle size of the majority of the particles or droplets formed by the nebulization is less than about 10 microns, about 8 microns, about 5 microns, or about 3 microns. For example, in some embodiments, about 60%, 70%, 80%, 90% or greater of the particles or droplets formed by the nebulization are less than about 5 microns. In these or other embodiments, the particles may be produced within a particle size dispersion wherein at least 50%, 60%, 70%, 80%, 90%, or 95% of the particles may be with about 3 microns and about 10 microns, about 3 microns and about 8 microns, about 3 microns and about 5 microns, about 5 microns and about 8 microns, about 5 microns and about 10 microns, or about 8 microns and about 10 microns.

Accordingly, a method of administering the topical composition comprising a nebulizer formulation may comprise using a small particle nebulizer delivery system and nebulizing the formulation to form small particles or droplets. The small particles may then be inhaled into the upper airway and deposit at the paranasal sinus and nasal mucosa. Compared to large particle nebulizer delivery systems, small particle nebulizer delivery systems may be used to deliver a greater fraction of active agents to the pulmonary system. This may increase systemic bioavailability of the active agents. However, when increased systemic bioavailability is not desirable, e.g., when such bioavailability is linked to unwanted side effects, the formulation may be prepared for and delivered by a large particle nebulizer delivery system. While any suitable small particle nebulizer delivery system or device may be used, one suitable device is a PARI or Sinustar intranasal nebulizer.

In one embodiment, the topical composition comprises a nebulizer formulation for delivery via a large particle nebulizer or delivery system. The large particle nebulizer delivery system may include a nebulizer configured to generate particles or droplets wherein the majority of the particles or droplets are larger than about 5 microns, about 10 microns, about 15 microns, about 20 microns or more, such as about 23 microns. In various embodiments, nebulization with a large particle nebulizer produces aerosol particles wherein the majority of particles are greater than about 10 microns, about 15 microns, about 20 microns, or about 25 microns. In these or other embodiments, the particles may be produced within a particle size dispersion wherein at least 50%, 60%, 70%, 80%, 90%, or 95% of the particles may be within about 10 microns and about 25 microns, about 10 microns and about 20 microns, about 10 microns and about 15 microns, about 15 microns and about 25 microns, about 15 microns and about 20 microns, or about 20 microns and about 25 microns. Accordingly, a method of administering the topical composition comprising a nebulizer formulation for large particle nebulization may comprises nebulizing the nebulizer solution to form large particles. The large particles may then be inhaled into the nasal and paranasal sinus cavities and for deposition on the frontal recess/sinus, sphenoethmoid recess, ethmoid cavity, sphenoid and maxillary sinuses, turbinates, middle meatus, and olfactory cleft. The large particle nebulizer delivery system may be configured to provide low volume, high concentration delivery of the formulation. An exemplary nebulizer device is a NASONEB® Nasal Nebulizer. Such large particle delivery systems may be employed to deliver a deep, penetrating aerosol to the nasal and paranasal sinus cavities of the patient. Such delivery may include little to no incidental pulmonary delivery of drugs, which may otherwise occur in small particle systems, as described above. For example, in some embodiments, large particle nebulization may provide superior outcomes compared to small particle nebulization to treat the upper respiratory tract, which typically include pulmonary delivery and decreased nasal and paranasal sinus cavity disposition.

In one embodiment, the large particle nebulizer system may be used to nebulize the nebulizer solution to generate large particles for delivery to the respiratory tract via a positive pressure airstream that ensures the components of the composition reach all of the desired nasal and paranasal sinus cavities. The large particle nebulizer system may preferably deliver the large particles such that they are readily filtered by the nose to ensure a large percentage of medication is delivered upon target surfaces where intended and that little or no unintended components of the formulation are delivered to the lungs, thus, reducing the risk of unwanted complications.

In one embodiment, the large particle nebulizer system is configured to deliver a low volume treatment solution comprising the composition to ensure that the active agents of the formulation stay in the nasal cavity. Accordingly, such a system may reduce waste generated by irrigation systems. In one embodiment, the large particle nebulizer system is configured to deliver 0.2-15 mL of nebulizer solution comprising the unit dose of active agents for retention in the nasal and paranasal sinus cavities. In one embodiment, the large particle nebulization system may also reduce complications associated with repeated exposure to cold fluid irrigation such as exostoses of the paranasal sinus cavities by warming the solution to near room temperature upon nebulization, which may help to avoid the iatrogenic complication of exostoses from cold fluid irrigation.

Administering the nebulizer treatment solution via a large particle nebulizer system may also avoid undesirable complications that may be linked to long term use of small particle nebulization systems, which may include vocal irritation/alterations, chronic cough, antimicrobial resistance, eosinophilic pneumonia, and reduced lung function.

According to one embodiment, the nebulizer formulation is configured for treatment of allergic rhinitis or other rhinologic conditions.

According to various embodiments, delivery of the formulation via a small particle size delivery system provides penetration of the formulation or its active agents into the lower respiratory tract.

The topical composition may also be configured for nasal administration via intranasal irrigation. In such embodiments, the typical mode of administration may be in flush form or liquid stream form. An example of suitable sinus rinse delivery mechanisms include the NEILMED® Sinus Rinse Bottle, a medical syringe of about 20 to about 60 ml in size, and other squeeze bottle irrigation devices. Typically, the formulation is administered two or three times a day. Various forms of irrigation may be used such as high volume, low volume, high pressure, low pressure, or combination thereof. For example, in some embodiments, the topical composition may be administered by low volume, low pressure irrigation. In another example, the topical composition may be administered by high volume, high pressure irrigation.

Effectiveness of the composition for treatment of respiratory tract conditions wherein the composition comprises a treatment solution administered via a NASONEB®, Sinustar, or irrigation system may provide advantages over conventional azelastine hydrochloride nasal spray compositions. For example, administration of the composition via intranasal nebulization, e.g., using a NASONEB® intranasal nebulizer, or with irrigation may provide the ability to increase positive pressure associated with such irrigation or nebulization. Also, if delivered via a large particle nebulization system including a large particle nebulizer device, the composition thereof will reach the paranasal sinus area in lieu of the frontal area where a nasal spray would reach thereby providing additional and enhanced benefits.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y".

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "about" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements disclosed herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of treating anosmia, the method comprising:
formulating a topical composition for topical nasal administration via nebulization or irrigation comprising:
combining a steroid, theophylline, quinine sulfate, and a diluent,
wherein the steroid comprises methylprednisolone and is combined in an amount about 1 mg to about 10 mg per unit dose,
wherein the theophylline is combined in an amount about 15 mg to about 250 mg per unit dose, and
wherein the quinine sulfate is combined in an amount about 50 mg to about 650 mg per unit dose; and
nasally administering to a subject the topical composition by intranasal irrigation or nebulization to treat anosmia.

2. The method of claim 1, further comprising combining poloxamers and xylitol with the steroid, theophylline, quinine sulfate, and diluent.

3. The method claim 1, wherein the diluent is an aqueous solution.

4. The method of claim 1, wherein the steroid further comprises fluticasone, and wherein the fluticasone is combined in an amount between about 0.5 mg and about 6 mg per unit dose, and wherein the theophylline is combined in an amount about 100 mg per unit dose.

5. The method of claim 1, wherein the steroid further comprises budesonide, and topical composition further comprises sodium chloride, disodium edetate, polysorbate 80, citric acid, tri-sodium citrate, and water for injection, and wherein the budesonide is combined in an amount between about 0.5 mg and about 4 mg per unit dose.

6. The method of claim 5, wherein combining the steroid comprises combining the contents of one or more budesonide 0.5 mg-2 ml vials and/or one or more budesonide 1 mg-2 ml vials, and wherein the theophylline is combined in an amount about 100 mg per unit dose.

7. The method of claim 1, wherein the methylprednisolone is combined in an amount about 5 mg, and wherein the theophylline is combined in an amount about 100 mg per unit dose.

8. The method of claim 3, wherein the diluent is a sodium chloride solution.

9. The method of claim 8, wherein the methylprednisolone is combined in an amount about 5 mg per unit dose, and wherein the theophylline is combined in an amount about 100 mg per unit dose.

10. The method of claim 9, further comprising combining poloxamers and xylitol with the steroid, theophylline, and diluent.

11. The method of claim 3, wherein the diluent is distilled water.

12. The method of claim 11, wherein the methylprednisolone is combined in an amount about 5 mg, and wherein the theophylline is combined in an amount about 100 mg per unit dose.

13. The method of claim 12, further comprising combining poloxamers and xylitol with the steroid, theophylline, and diluent.

14. The method of claim 13, wherein the steroid further comprises flurandrenolide.

* * * * *